United States Patent [19]
Peleg

[11] Patent Number: 4,884,696
[45] Date of Patent: Dec. 5, 1989

[54] METHOD AND APPARATUS FOR AUTOMATICALLY INSPECTING AND CLASSIFYING DIFFERENT OBJECTS

[75] Inventor: Kalman Peleg, Washington State University, Department of Argicultural Engineering, Pullman, Wash. 99164

[73] Assignee: Kaman Peleg, Haifa, Israel

[21] Appl. No.: 170,307

[22] Filed: Mar. 21, 1988

[30] Foreign Application Priority Data

Mar. 29, 1987 [IL] Israel ......................................... 82037

[51] Int. Cl.$^4$ .......................... B07C 5/02; B07C 5/07; B07C 5/08; B07C 5/10
[52] U.S. Cl. .................................... 209/545; 209/576; 209/580; 209/588; 209/589; 209/593; 209/599; 209/602; 209/912; 198/408
[58] Field of Search ............... 209/555, 560, 576, 577, 209/580, 588, 589, 592, 593, 600–602, 599, 538–545, 912, 939; 198/408; 358/101, 106; 271/204, 186

[56] References Cited

U.S. PATENT DOCUMENTS

| | | | |
|---|---|---|---|
| Re. 25,894 | 11/1965 | McGrath | 209/560 |
| 4,050,574 | 9/1977 | Chenevard et al. | 198/458 |
| 4,061,020 | 12/1977 | Fridley et al. | 73/81 |
| 4,082,188 | 4/1978 | Grimmell et al. | 209/580 X |
| 4,106,628 | 8/1978 | Warkentin et al. | 209/593 |
| 4,135,619 | 1/1979 | Cerboni | 271/186 |
| 4,221,297 | 9/1980 | Aranda Lopez et al. | 209/576 |

Primary Examiner—Joseph J. Rolla
Assistant Examiner—Steven Reiss

[57] ABSTRACT

Univeral conveying apparatus and method for automated inspection and classification of a variety of natural or man made product classes, having various geometrical configurations, e.g. spheroidal, spherical, cylindrical, parallelepiped, disc and plate shaped objects, or massive and hollow amophous objects. Incorporating a plurality of sensors interfaced to a plurality of microcomputers, measuring different product features, while predetermined combinations thereof are used for separating the objects or products, into a plurality of categories. Part of the sensors are stationary, while another part thereof are located and rotating on revolving inverter wheels. The stationary and rotating sensor groups are interfaced respectively to one or more stationary or rotating microcomputers, attached to the inverter wheels. The revolving and stationary microcomputers are electrically interconnected via slip rings, on the shafts on the inverter wheels. Conveing system incorporates product inversion, providing means for computer vision of both sides of rapidly moving objects or products, on two synchronized bottomless cup or tray conveyors, stacked one on top of the other, while the inverter wheels with reciprocating product grippers, transfer and invert inspected objects, from one conveyor to the other. Combines computer vision by reflected and/or transmitted radiation, with self radiation if any, in concert with other sensors. Some sensors in the grippers, intermittently contact or engage objects in cups or trays, by a controlled force or pressure. The grippers may be rigid, flexible or semiflexible. They may incorporate actuators and sensors for measuring mechanical properties of products and probe connectors for electrical functionality analysis.

25 Claims, 11 Drawing Sheets

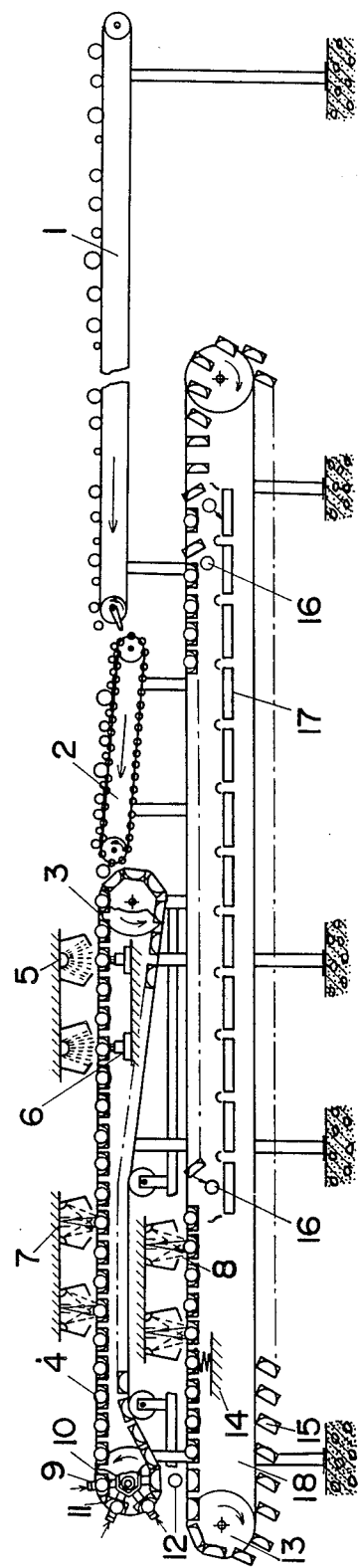
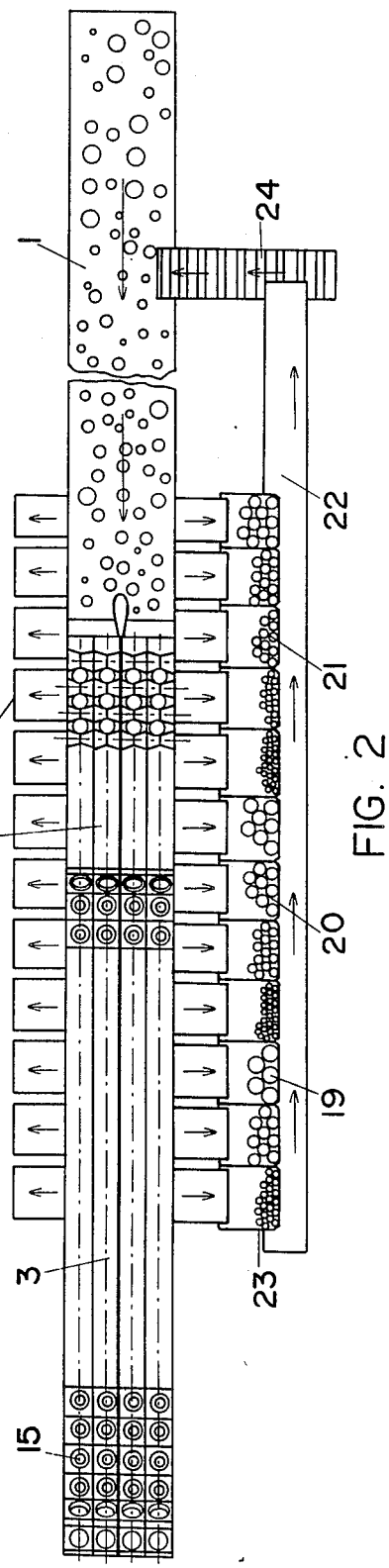
FIG. 1
FIG. 2

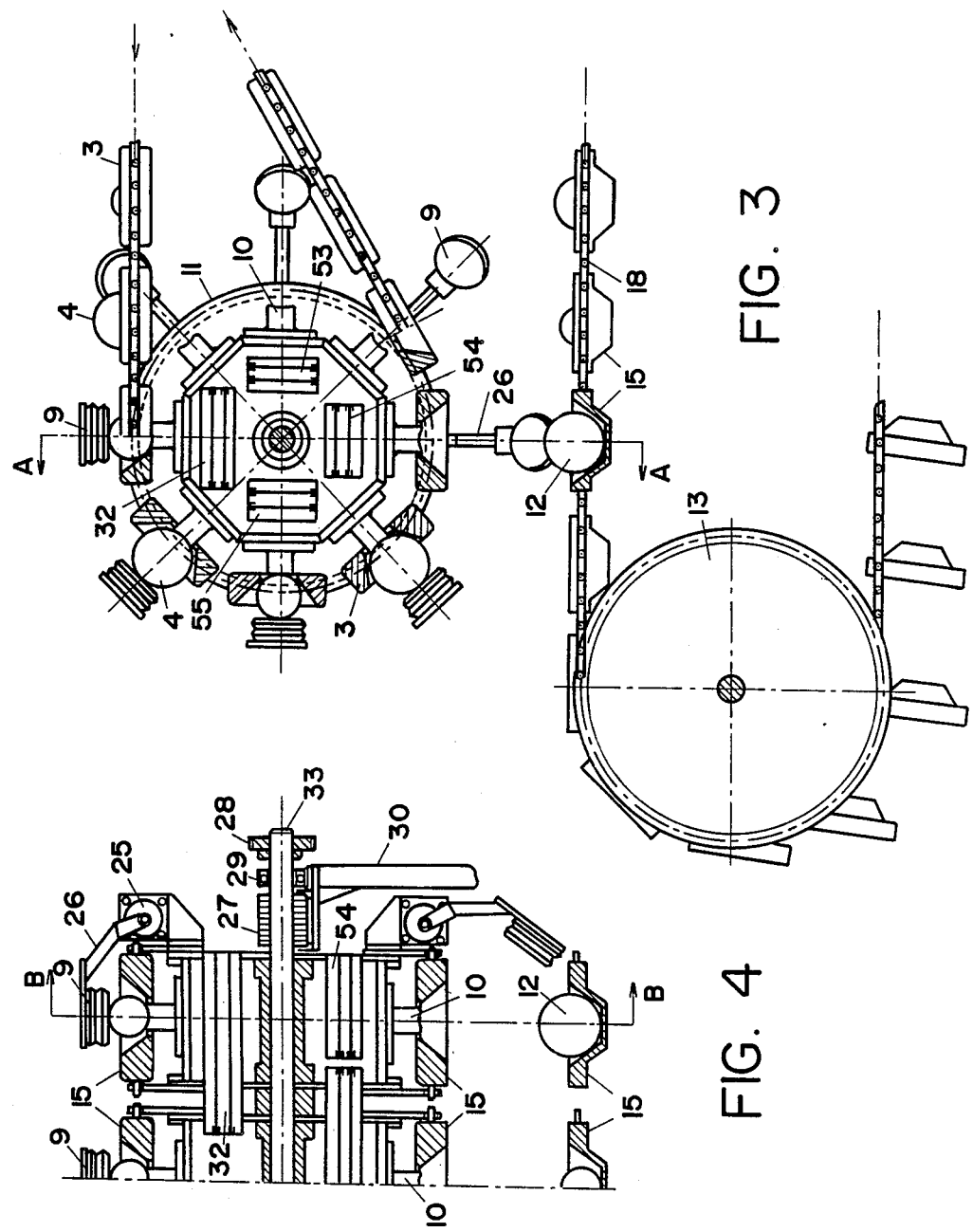

METHOD AND APPARATUS FOR AUTOMATICALLY INSPECTING AND CLASSIFYING DIFFERENT OBJECTS

BACKGROUND OF THE INVENTION

1. Field of the Invention

This invention relates to a method and universal conveying apparatus for automated inspection and classification of a variety of different product classes, while using a plurality of sensors interfaced to computer means for measuring different product features and separating same into predetermined categories. Following are some examples of product classes that can be conveyed, inspected and classified:

a. Spherical and spheroidal objects such as fruits and vegetables, ball bearings, billiard and bowling balls and the like.

b. Cylindrical objects such as cans, bottles, jars, drug capsules, cigarettes, ordnance shells, bullets, and the like.

c. Disc shaped objects such as wheels, gears, bottle or jar closure caps, round plates, cakes, precooked meals or pizzas in aluminum foil trays, tablets and the like.

d. Parallelepiped shaped objects such as boxes and containers (empty or with variously packaged items within), box-shaped various manufactured products, small appliances, components and parts.

e. Plate shaped objects such as electronic printed circuit boards.

f. Amorphous objects such as dates, berries, potatoes, avocado, soil clods, radioactive ore pieces, cookies, bread and other bakery products.

2. Description of Prior Art

Most existing automatic inspection machines are designed to classify or sort only a particular product class, and in most cases the classification is based on a single product feature. When more than one feature is used (usually less than three), they are addressed serially, one at a time, by one or several machines in a row. Of all products that can be efficiently inspected and classified by the machine disclosed hereby, sorting and sizing fresh fruits and vegetables is one of the most demanding and difficult tasks.

Color sorting machines for various specific fruits and vegetables, using yellow/green, red/green, blue/green etc. light reflectance ratios, have been used commercially for many years. The operating principle of these machines was based on optical filtration of reflected light, while the classification decision was performed by analog circuitry. Analog circuit color sorting is usually specific for each particular fruit type. It has largely been made obsolete by the introduction of digital image processing, such as in the machine disclosed herein, whereby color sorting is just one of several product features detected by reflected light, i.e. size, shape and surface blemishes.

The key component of any inspection machine, designed to sort a stream of objects in a mass production environment, is the conveying system. Its main function is to efficiently carry and present the inspected objects to the sensors. Three main types of conveying systems have been used hitherto in inspection machines based on computer vision:

a. Flat belt conveyors.
b. Cup conveyors.

The disadvantage of these conveyors is that the underside of the objects carried on them can not be seen by the camera. The flat belt conveyor has an additional deficiency since the exact placement of the objects on it is not known.

c. Roller conveyors, as in (1980 U.S. Pat. No. 4,221,297), which strive to overcome the above deficiencies by rapidly spinning spheroidal objects such as fruits, in front of a line scan camera.

Another popular way of presenting all sides of an object to a set of cameras is to view it simultaneously from different angles, as it free falls in a projectile like trajectory from one conveyor to another.

Inherent inaccuracy of this method stems from inconsistency of object orientation due to variability in sizes and shapes, while significant damage may be incurred by sensitive products, e.g. fruits and vegetables. Rapidly spinning a product in front of a line scan camera has essentially the same disadvantages, since it is very difficult to ascertain exactly one revolution view when the products vary in size and shape. Rapid spinning may also damage a delicate products.

The above conveying and inspection principles comprise "Reduction Sorting", whereby diversion mechanisms selectively deflect different product fractions form the main product stream, usually based on a single feature, e.g. color, blemishes, size etc. Even if more than one feature is inspected, it is done so serially by different machines, i.e. a color grading machine is followed by a sizing machine, while grading is mostly manual. The diversion mechanism is usually a solenoid operated baffle or an air stream blast. In most cases further inspection is required to finalize product grading according to other product features, by additional machines or human inspectors. In contrast, the machine disclosed hereby performs "Full Sorting" whereby several features of each and every piece are inspected, while a Bayesian type multiple feature decision-making algorithm may be used to optimally classify the product, whereupon it is deposited onto the appropriate side delivery conveyor. Needless to say that the former method is less cost effective.

The machine disclosed herein allows viewing and inspection of opposite sides of an objects at high speed by means of a pair of stacked cup conveyors and retaining grippers which hold the objects in place while they are turned around by an inverter wheel, as described in detail in the preferred embodiment of the present invention. This inversion apparatus is different and superior to the dual drum arrangement for capsule color sorting, as described in (1978 U.S. Pat. No. 4,082,188).

Another case in point is sorting by specific gravity, such as may be used for separating freeze damaged oranges from wholesome fruit, thick skinned fruit from thin skinned fruit, potatoes from soil clods etc. The machine disclosed herein can determine specific gravity of each inspected piece by its weight and volume, in conjunction with a plurality of other features.

In addition to the above product properties, it is sometimes also required to classify products by their mechanical or rheological properties. Thus a patent has been granted for an elaborate single feature machine which produces indentations on fruits for assessing their firmness, (1977 U.S. Pat. No. 4,061,020). Here again, the preferred embodiment of the present invention provides several superior means for measurement of mechanical properties of the inspected products, i.e. resistance to applied forces, contact pressure, frequency response or vibration damping characteristics and internal energy dissipation "on the go", without stopping the conveyor belt or reducing throughput speed.

In summary, we may cite the following deficiencies of commercially available inspection and classification machines:

a. The conveying apparatus of each machine is suitable for inspecting only a particular product class. This precludes cost effective standardized mass production, wherein adaptation to different products is only a matter of choosing the appropriate sensors and software package, while the structure of the machine and most of its mechanical parts remain the same.

b. While classifying only a specific product, the further restriction to one or at most two or three product features constitutes "Reduction Sorting", capable in most cases of performing only part of the entire sorting task, while the remainder is performed manually.

c. There is no provision for viewing both sides of an object while it rests upon a rapidly moving conveyor, enabling "Computer Vision Inspection" including reflected as well as transmitted radiation types, in conjunction with a plurality of other sensor systems.

d. There is no provision for accomplishing c. while handling the product gently, thereby minimizing potential mechanical damage to delicate products.

e. There is no means for physical contact with the inspected products "On-The-Go" whereby electrical connectors can be automatically attached to the product for functionality inspections.

f. There is no means for measurement of mechanical properties of inspected materials or products, wherein it may be important to measure resistance to applied forces, contact pressure, frequency response or vibration damping characteristics and internal energy dissipation, without stopping the conveyor or reducing throughput speed.

SUMMARY OF THE INVENTION

It is therefore an object of the present invention to provide a novel universal conveying apparatus for presenting both sides of objects or products to reflective and penetrating radiation sensors, in concert with other sensor types and particularly retaining grippers and sensors for contacting inspected items while measuring their mechanical properties and or electrical funtionality, as well as methods and computing hardware, for implementing Bayesian type optimal multifeature automatic inspection and classification into predetermined grades, while being easily readjustable for performing the above on a plurality of different product classes.

The main tool in automatic inspection is "Computer Vision", whereby a digitized video camera image of an item is processed by a computer. Computer manipulation of the digitized image provides a means of extracting distinguishing features which may serve for categorizing or classifying the product. Apart from the visual light spectrum used by human inspectors "Computer Vision" may include other types of reflected radiation, e.g. Infra Red or Ultra Violet light, or transmitted radiation, when hidden attributes of a product are inspected via X-rays, Y-rays, Lasers or NMR. To be cost effective, automated inspection must be performed at high speed, while all sides of the product are presented to the camera and a plurality of other sensors.

To detect reflected radiation, the machine disclosed hereby provides a simple means of viewing both sides of objects i.e. two 180 degree viewing angles, while they are consecutively transported on two cup conveyors, stacked one on top of the other. An inverter wheel incorporating special grippers, transfers the conveyed objects from one cup conveyor to the other while inverting same. Suitable openings in the bottoms of the cups or rays permit detection of transmitted radiation, through two opposite sides of an object. Self emitted radiation from both sides of an object can also be detected, which is particularly advantageous in automatic radiometric inspection of radioactive ores.

A further desirable feature of this machine is the ability to transport and invert the object, while handling it gently, thereby minimizing potential mechanical damage to delicate products such as fruits and vegetables, processed food products, or fragile parts and components of manufactured products.

Most manual inspection procedures comprise classification of products based on several distinguishing features simultaneously e.g. manufacturing or material defects, electrical functionality, blemishes, geometrical patterns, colors, dimensions, size, shape, weight, firmness, surface roughness etc. To imitate and surpass human inspectors capabilities, the machine disclosed hereby, enables multifeature/multisensor inspection without reducing the throughput speed or increasing potential product damage.

Apart from visually viewing the product, human inspectors may also pick up inspected products while gently squeezing them with their fingers to asses firmness, e.g. fruit ripeness, its maturity or decay. Processed food products may have to be similarly handled for estimating their rheological properties.

Inspection of manufactured products may also require measurement of mechanical properties, such as resistance to applied forces, contact pressure, frequency response or vibration damping characteristics and internal energy dissipation. The multiple sensing inspection and classification machine disclosed hereby affords automatic measurement of such mechanical properties "on the go", without stopping the conveyor belt or reducing throughput speed. Nevertheless a "stop and go" intermittent conveyor motion may be utilized, whenever a mechanical properties inspection of a product requires that the actuators remain stationary during the test, such as in relatively longer MIL-SPEC's vibration response tests.

In some cases the inspection of a product also requires an operational functionality check, wherein a power source is connected to the product, while electrical signals emanating from it are indicative of its proper or faulty operation. A case in point are electronics printed circuit boards and IC chips mounted thereon. The conveying apparatus of the present invention also supports implementation of probe connectors, which can be automatically attached to selected leads, junctions or to the edge connector of the circuit board on-the-go. Thus, while both sides of the board are inspected by computer vision, the appropriate tell-tale signals may be analyzed in the same time, by the inspection machine's computer to assess its functionality.

Many product classification features may be statistically distributed, while high speed automatic inspection requires classification based on only one or a limited number of measurements of each feature. To minimize classification errors, the present machine includes computing hardware for implementing Bayesian type multifeature decision making computer algorithms developed by the inventor, which may significantly enhance classification accuracy. These may include, on line continuous sampling and statistical inference as to the probability densities of the inspected and the classified products, while assessing the probabilities of classification errors i.e. the accuracy of the machine. These classification error probabilities may then be used as feedback data to said machine learning algorithm enabling automatic optimal classification scale adjustment. To further improve classification accuracy in terms of consistency, repeatability, and enhance optimal calibration of the feature measuring devices and sensors, the present machine features an array of classified products sampling stations. By periodically sampling and manual close precise inspection of the classified products, one can verify correct sensor calibrations and assess the actual classification errors or accuracy of the machine.

In summary, the most important novel key components of the present multiple feature inspection and classification machine are:

1. Product Inversion Conveying System. Comprising two chain conveyors with cups or trays attached thereon, stacked one on top of the other, while a special inverter wheel with object grippers is used to gently transfer said objects from the end of said top conveyor to the beginning of the said bottom conveyor, while simultaneously inverting same. To further enhance access to both sides of a product, the bottoms of said cups or trays may incorporate differently shaped apertures. The main function of this system is to provide a means of viewing both sides of objects while they rapidly move in evenly spaced rows, in said cups or trays, in a continuous motion or in a stop-and-go intermittent mode. The system handles the product gently, thereby minimizing potential mechanical damage to delicate products. This affords improved inspection by "Computer Vision", utilizing reflected and/or transmitted radiation, as well as self radiation emitted by the inspected object, if any.

Another unique feature of this conveying system is the provision for product classification based on several distinguishing features simultaneously (including mechanical properties), by enabling multisensor inspection without reducing the throughput speed or increasing potential product damage. It also enables "Full Sorting" rather than "Reduction Sorting" of products whereby each piece is deposited or transported to its assigned destination, according to a plurality of predetermined features.

In addition to the above, this conveying system also provides a means for periodically sampling and close precise inspection of the classified products, enabling assessment of the actual classification errors or accuracy of the machine. These classification errors are then used as feedback data to a computer algorithm enabling optimal classification scale calibration and automatic adjustment or resetting.

2. Stepper Motor Driven Revolving Object Retaining Grippers.

In addition to retaining the product in the cup or tray by a controlled force or pressure during the object inversion stage as described above, the grippers may be outfitted with electrical probe connectors for product functionality analysis.

Different gripper configurations may be easily implemented to suit a wide variety of product classes. Rigid or flexible grippers may be used, depending on product type and inspection task at hand. They may incorporate different sensors, providing a means for measuring the mechanical properties of the inspected products. Depending on the sensor type used, resistance to applied forces, contact pressure, frequency response or vibration damping characteristics and internal energy dissipation may be measured "on the go", without stopping the conveyor or reducing throughput speed. Intermittent stop-and-go conveyor motion may also be easily implemented, if the inspection task at hand so requires.

When outfitted with a force load cell, the rigid gripper is most useful for measuring quasi-static force-deflection characteristics of the inspected product, in order to assess its mean stiffness. When pressure-deflection is desired, or when it is required to obtain information about the contact surface characteristics and pressure distribution thereon, a tactile sensor may be employed in place of the load cell.

3. Rotating Vibration Actuators and Associated Sensors.

Electrodynamic and or Piezoelectric vibration actuators may be mounted on the periphery of the inverter wheel, for applying vibration excitation to the objects, through the apertures in the bottoms of the cups or trays. In conjunction with flexible grippers and associated sensors, this permits measuring mechanical product properties by dynamic loading, e.g. measuring product vibration response characteristics in a wide range of frequencies.

Low frequency excitation in the subsonic range, is provided by an electrodynamic actuator. Input and output acceleration, to and from the product is measured by an electronically matched pair of acceleration transducers, mounted in the vibration actuator head and in the gripper. A flexible finger gripper in the form of a leaf spring may be additionally instrumented with strain gauges for measuring the gripping force and dynamic response of the vibrationally excited object. The signals from the acceleration transducers and other sensors are fed into an electronics package mounted on and revolving with the inverter wheel, providing signal conditioning and amplification as well as measurement of relative displacement, power and energy dissipation in the product. High frequency energy in the sonic and ultrasound band may also be applied to the product and measured simultaneously or separately by a piezoelectric actuator, which may be attached to the end of the electrodynamic vibration actuator.

4. Automatic Product Sampling Stations for Machine Training Sets, Enabling Optimal Classification Scale Calibration and Adjustment.

A means is provided for automatic sampling and manual close precise inspection and feature measurements, of trial sets of classified products samples. This data comprises updated machine training sets whereby the actual classification errors or accuracy of the machine may be automatically computed. These classification errors are then used to automatically calibrate or readjust the classification scale settings, i.e. update the lookup tables in the decision-making computer algorithm.

BRIEF DESCRIPTION OF THE DRAWINGS

FIG. 1 shows a side view of the general layout and conveying system of the multiple sensor computerized inspection and classification machine.

FIG. 2 shows a top view of the general layout and conveying system of the multiple sensor computerized inspection and classification machine.

FIG. 3 is a cross section along line BB in FIG. 4, showing side view of cup conveyor, inverter wheel and revolving product grippers. This configuration exemplifies a cup-gripper configuration, most suitable for spheroidal or spherical objects, such as fruits or vegetables.

FIG. 4 is a cross section along line AA in FIG. 3.

DETAILED DESCRIPTION OF THE PREFERRED EMBODIMENT

1. Structure and Operation

Figure 5:
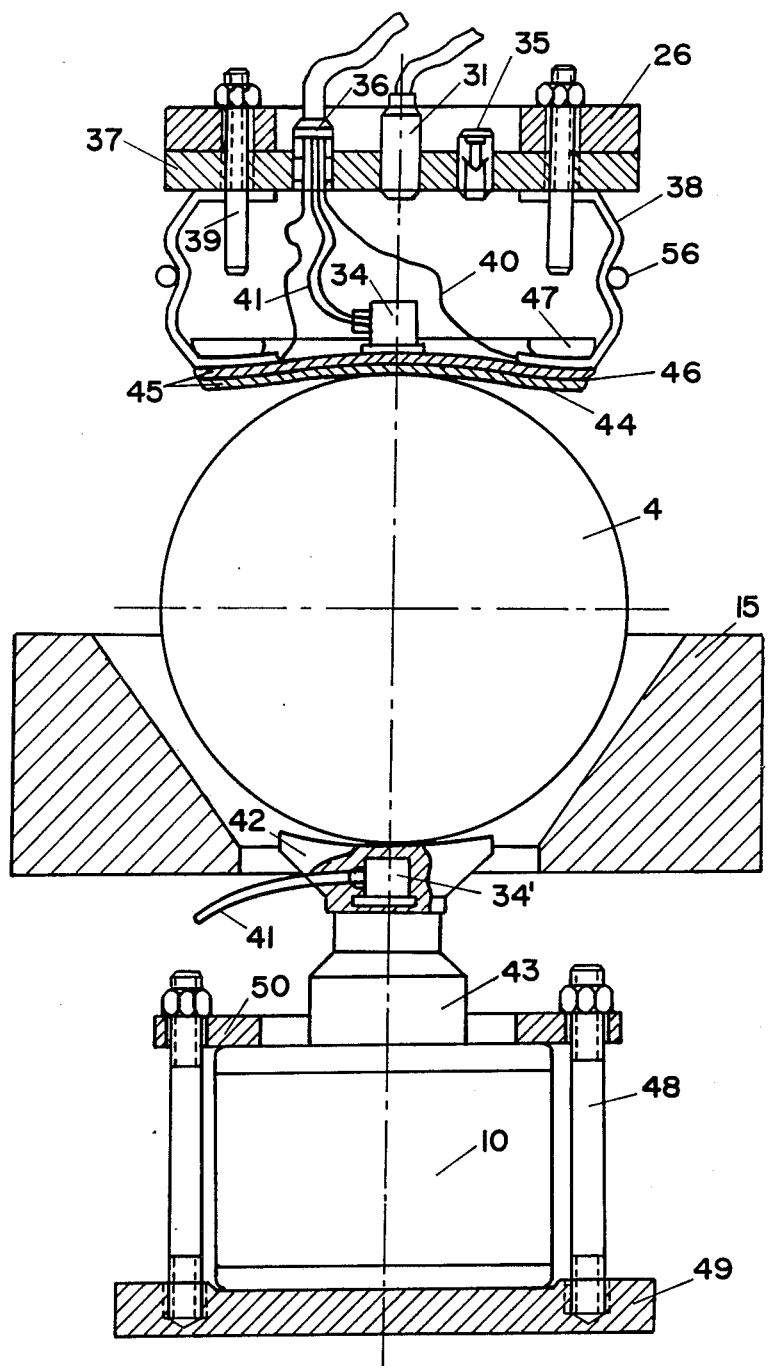
FIG. 5 shows vibration actuator and cup cross section with flexible gripper and associated sensors, for inspecting spheroidal or horizontally placed cylindrical objects, such as a fruits or tin cans.

The general embodiment of the invention comprising the conveying systems layout, of the multiple sensor computerized inspection and classification machine are shown in FIG. 1 and FIG. 2. This configuration of the machine, is particularly suitable for inspection and classification of fruits and vegetables according to size and quality grades, i.e. simultaneous grading and sizing. Nevertheless the basic features and principles incorporated in this version are readily adaptable to a wide variety of other products as well, by appropriate choice of singulating means, cup-gripper configuration, sensors and software options.

In operation a stream of objects, examplified herein by fruits, is delivered to the machine by a suitable means such as a conveyor belt (1), followed by a singulator grommet roller conveyor (2), which arranges the objects into evenly spaced rows.

From the singulator roller conveyor (2) the objects (4) are delivered into specially shaped cups or trays (15) of the upper cup-conveyor (3). For non-spheroidal and non-cylindrical objects, which can not roll, another type of appropriate singulating mechanism would have to be employed, for placing the products into said trays or cups. Depending on the product type and inspection task at hand, the bottoms of the cups or trays may or may not have variously shaped apertures, as explained in detail later.

The arrows on the delivery conveyor belt (1), singulator conveyor (2) and the upper cup-conveyor (3) show the direction of inspected objects movement from right to left. As the objects (4) travel in the cups or trays of the upper cup-conveyor (3), they pass by a plurality of inspection stations such as (5), (6) and (7), each measuring a different product feature.

In the first group various radiation sources (5), which have the capability to penetrate the inspected objects (4), are used in conjunction with suitable sensors (6) viewing the objects from beneath, through the apertures in the bottoms of said cups or trays (15). The attenuation pattern of the radiation transmitted through the objects (4) as detected by the sensors (6) is correlated to specific internal product features or defects, by a suitable pattern recognition computer program. Examples of radiation types which may be employed are X-rays, Y-rays, Lasers etc. If an object is not detected in a given cup, a flag is set in the controlling computer (block ** in FIG. 12), to signal the rest of the inspection stations to ignore it, i.e. to pass it without inspection.

When self emitting objects, such as radioactive ore pieces are inspected, there is no need for a radiation source and both (5) and (6) may comprise detecting devices, for classification by the emitted radiation from both sides of the ore piece.

The second group of inspection stations (7), comprise reflected radiation sensors e.g. visible light, ultraviolet light, infrared light etc. which can be reflected from the upper sides of the objects in the cups (15). These may be used for detecting the color of the object, external defects, unique geometrical patterns or various blemishes on its surface, dimensions, shape, contour, surface roughness, presence and proper mounting of components etc.

The third group of sensors in the product grippers (9) and vibration actuators (10), located on the inverter wheels (11), comprise a means for measuring the mechanical properties of a product.

An enlarged and more detailed view of a cup inverter wheel (11) and object grippers (9) is shown in FIGS. 3 and 4, while the exploded views in FIGS. 5, 6, 7, 8, 9, 10 and 13, examplify several gripper-cup configuration possibilities and associated sensors.

Consider first the object inversion operation only, leaving for later, the detailed description of the simultaneously executed inspections, while the cup or tray hugs the periphery of the inverter wheel (11).

Figure 6:
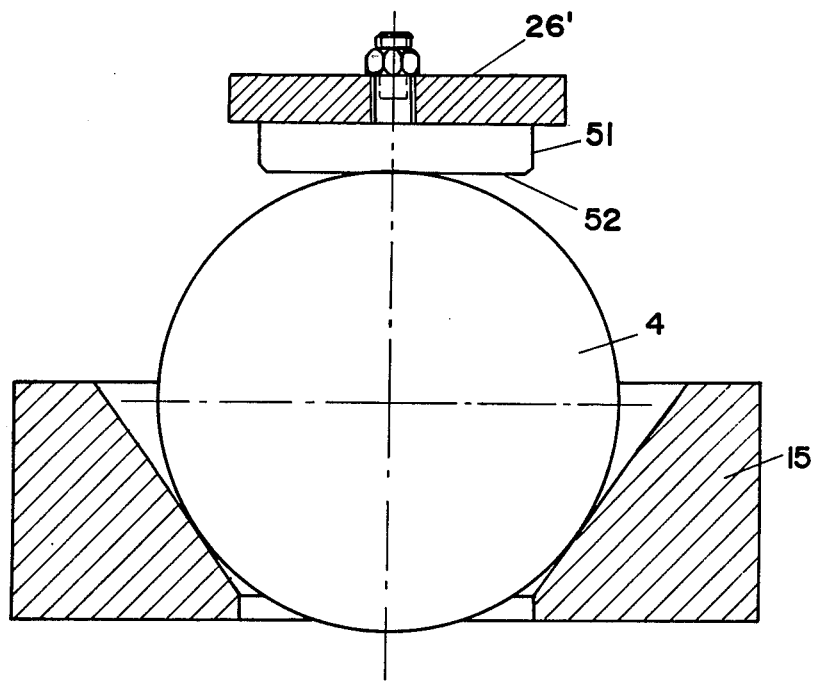
FIG. 6 shows cup cross section for similarly shaped objects as in FIG. 5, but with rigid gripper, incorporating tactile sensors.
Figure 7:
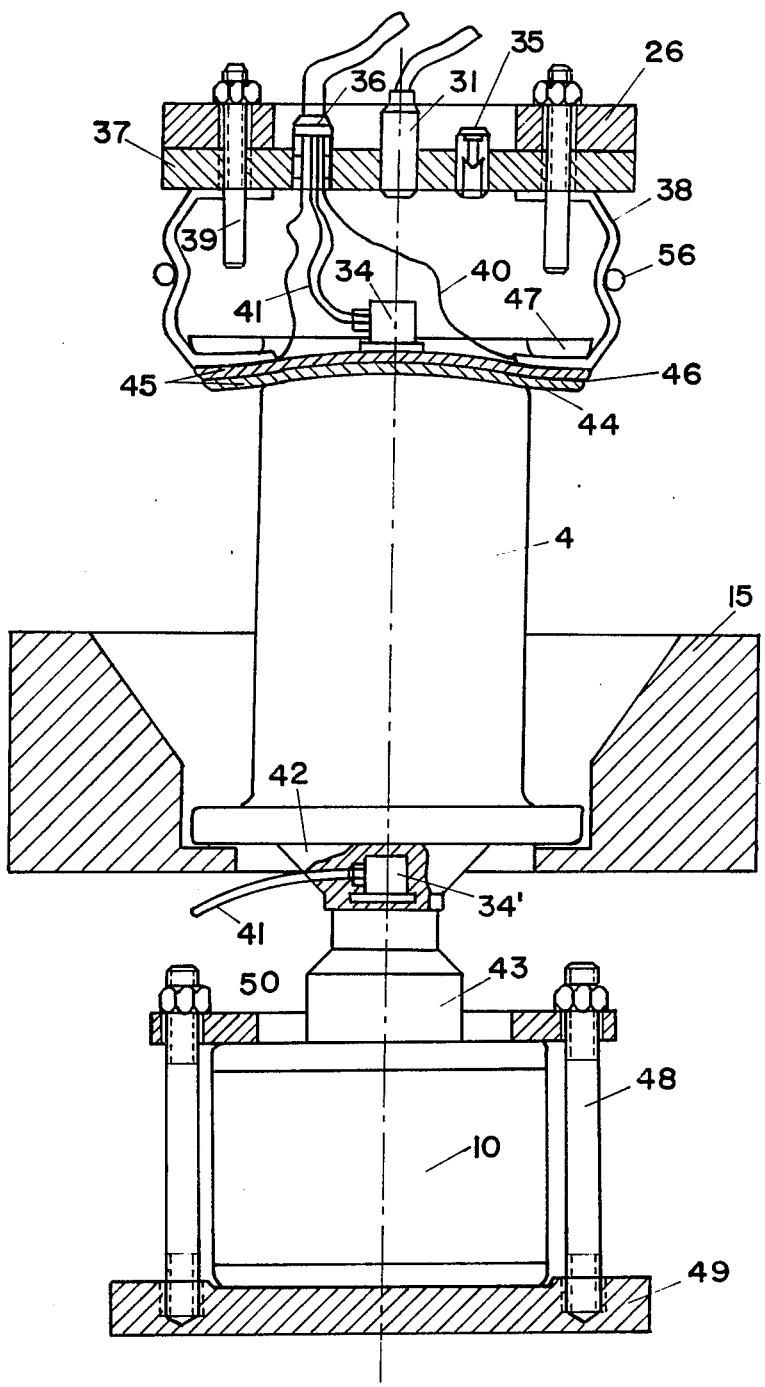
FIG. 7 shows vibration actuator and cup cross section with flexible gripper and associated sensors, for inspecting parallelepiped or upright placed cylindrical objects.
Figure 8:
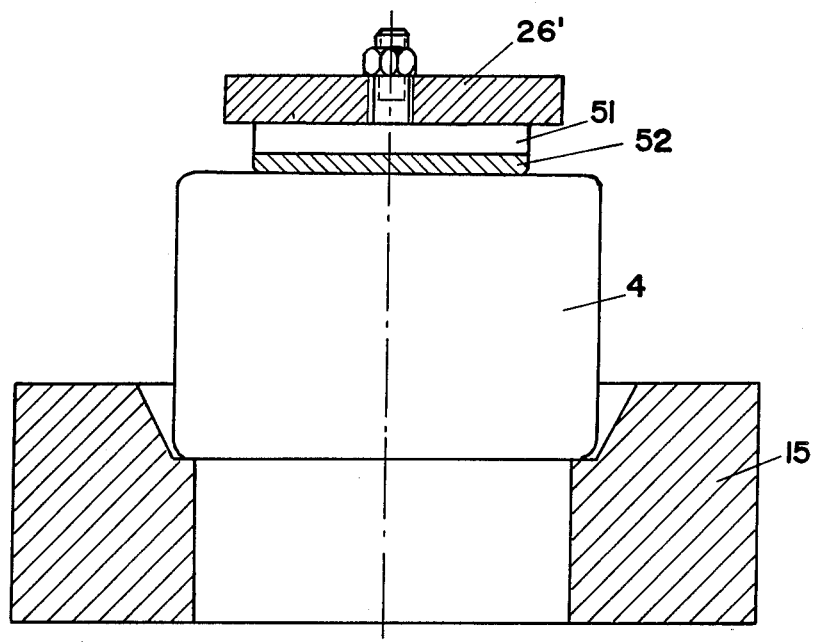
FIG. 8 is a tray cross section for similarly shaped objects, as in FIG. 7 but with rigid gripper incorporating tactile sensors, and or a load cell.
Figure 9:
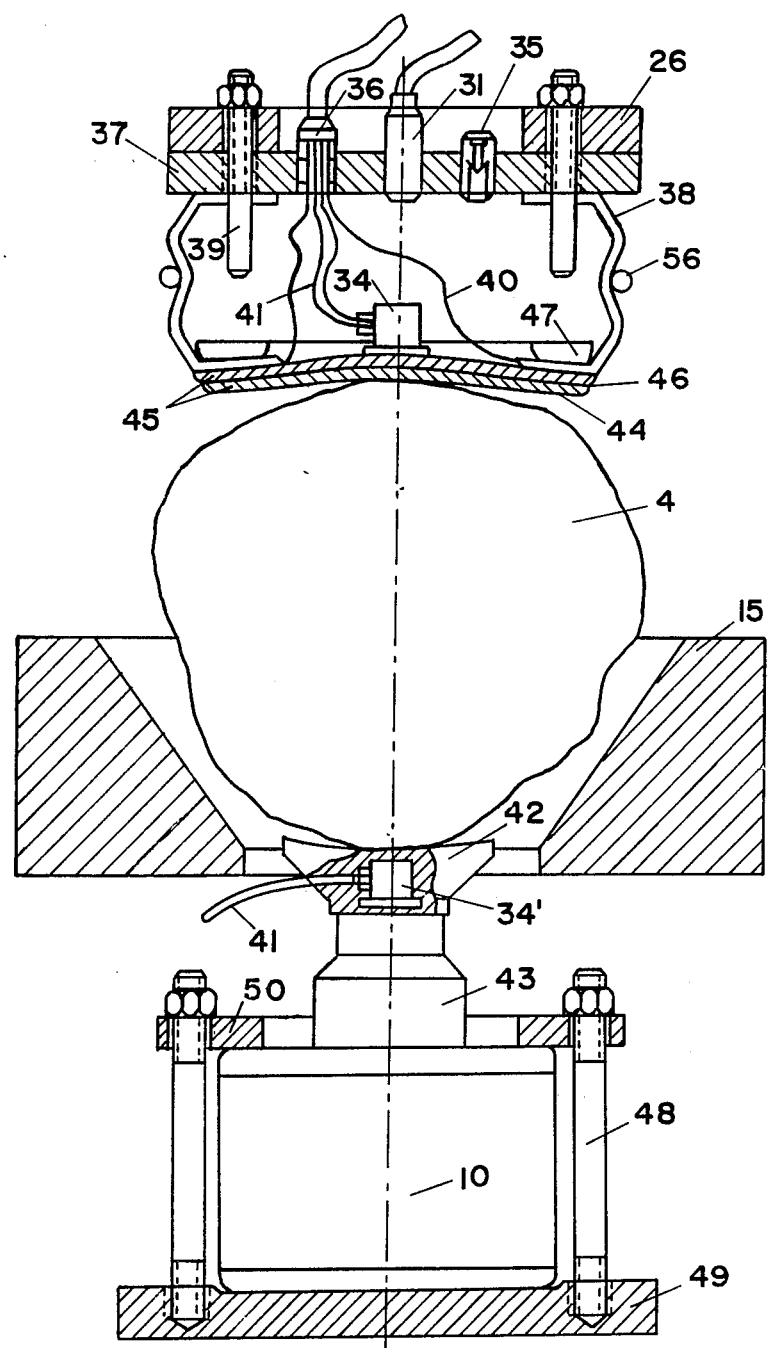
FIG. 9 is similar to FIG. 5 but examplifies inspection of an amorphous object.
Figure 12:
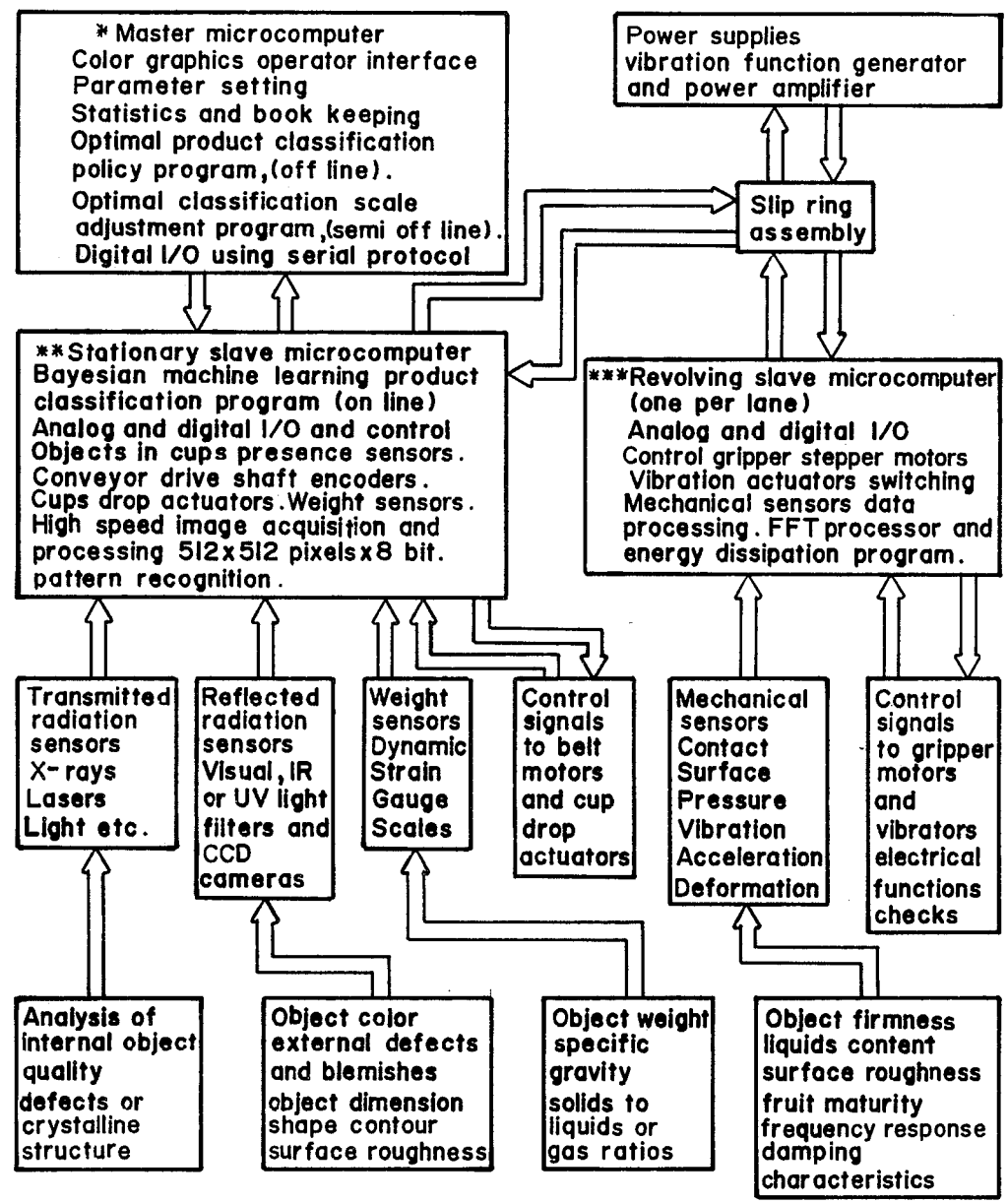
FIG. 12 Shows functional block diagram of computing and control hardware and software for the various sensors, drive motors, grippers and vibration actuators.
Figure 13:
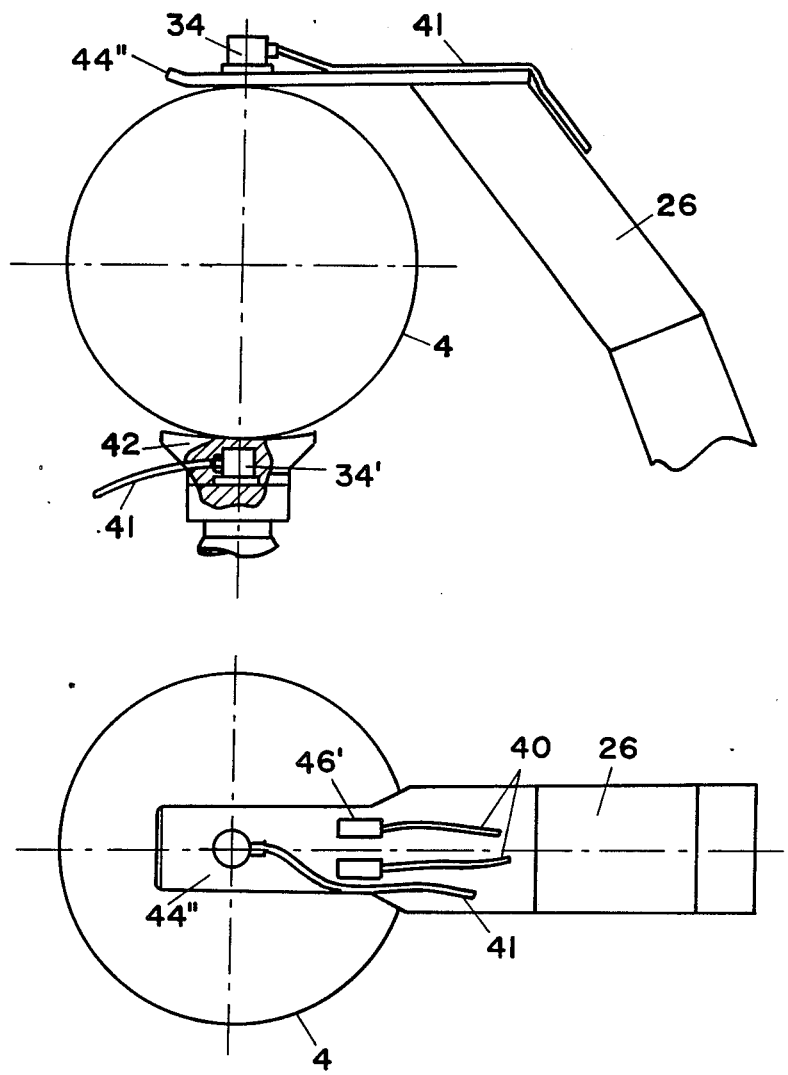
FIG. 13 Shows a flexible finger gripper configuration in the form of a leaf spring instrumented with acceleration transducer and strain gauges for simultaneously measuring output acceleration and gripping force.

Referring to FIGS. 1, 2, 3, 4 and the examples of cup-gripper and tray-gripper configurations in FIGS. 5 through 10 and 13, it is seen that as the conveyor (3) carrying the objects (4) in the cups (15) approaches the top of the inverter wheel (11), the gripper arm (26) or (26') driven by the stepper motor (25) quickly rotates until the gripper pad (44), (44'), (51) or leaf spring (44") contacts the object (4). If the object-in-cup absence flag is set for a given cup, the stepper motor (25) rotates the gripper arm (26) or (26') to a preset fixed position, approximating an average object size. If an object is present in the cup, the first contact point between the gripper and the object may be detected by five different means i.e. by the flexible gripper pad sensors (46) in the gripper pads (44) or pressure transducer (31) as shown in FIGS. 5, 7, and 9, or by the strain gauges (46') on the flexible finger gripper as shown in FIG. 13, or by one of the tactile sensor's sensitive sites (52) as examplified in FIGS. 6 and 8, or by the establishment of electrical contact by probes on the gripper pad (44') as examplified in FIG. 10 Once the first contact point is detected further movement of the gripper arm (26) or (26'), proceeds at a slower rate until the object (4) is retained in the cup (15) by a preset maximal force or pressure, which is known to be uncapable of inflicting damage to the inspected object. Usually this maximal force or pressure is only large enough to retain the object (4) in the cups (15) as the inverter wheel rotates the cup from the top to the bottom position, approximately 180 degrees. At this point the stepper motor (25) is reversed quickly, whereby the gripper (9) gently deposits the inverted object (12) into a corresponding cup or tray (15), in the lower cup-conveyor (18), as examplified in FIGS. 3 and 4. To assure precise cup synchronization for gentle and accurate deposition of the object, both the inverter wheel (11) and lower cup-conveyor drive wheel (13) are driven by synchro-motors controlled by the stationary slave computer, (block  in FIG. 12). The gripper arm stepper motors (25), on the other hand are controlled by smaller slave microcomputers (32) mounted on the inverter wheels (11), (one per inverter wheel, see block * in FIG. 12). A subsequent section of this disclosure, contains a detailed description of the operation and peripheral hardware implemented by the stationary slave microcomputer and the slave microcomputers mounted on the inverter wheels, as well as the master microcomputer incorporating the operators interface software module.

The arrow on the lower cup-conveyor drive wheel (13) denotes that the lower cup-conveyor (18) moves in the opposite direction of the upper cup-conveyor (3). Thus the inverted objects move to the lower reflected radiation inspection stations (8), whose construction is identical to stations (7), located above the upper cup-conveyor (3), as described above.

This arrangement permits inspection of both sides of variously shaped objects precisely, by different computer vision systems. A continuous conveyor motion mode is provided, wherein a line-scan camera may be employed for inspection of fast moving objects. An alternative intermittent stop-and-go conveyor motion mode is also available for employing frame-scan cameras, whereby the product is kept stationary during the frame grabbing time interval. Computer vision inspection employing transmitted radiation types, using line or matrix detector arrays may similarly be employed in the two conveyor motion modes. Such mode of computer vision inspection is much more efficient than spinning a object in front of a line scan camera, for viewing its entire surface, as utilized in some produce sorting machines or conventional inspection schemes of cylindrical objects, e.g. products in cans, bottles or jars.

Inspection station pairs (5) and (7) or (7) and (8) may also be combined for object inspection by delayed light emission. To this end the objects may be irradiated at inspection stations (5) or (7), while the light emitted from them after the delay is detected at stations (7) or (8) respectively.

Inspection stations (14) provide a means for weighing the products in the cups or trays on-the-go, as may be desirable in produce sorting. They comprise load cells, such as strain gauge bridges acting as force transducers for measuring the weight of each cup or tray, i.e. their output signals are proportional to product mass, while volume or size may be computed if the specific gravity and geometrical shape of the product is known. Cup or tray weighing may be implemented on the lower conveyors (18), before or after the lower reflected radiation inspection stations (8), wherein the cups or trays are hinged and incorporate sliding surfaces on their undersides corresponding to the said strain gauge bridges (14). Note that both cup-conveyors (3) and (18) may be made long enough to accommodate various additional product feature measuring devices or sensors, not explicitly mentioned herein.

After all the desired product features have been measured and the data assimilated in the memory of the stationary slave microcomputer (block ** in FIG. 12), a suitable program determines the product category and executes a command signal for tripping the cup (15) over the appropriate side delivery conveyor (17) carrying the classified objects (16). Most suitable for this task is a special Bayesian type machine learning multiple feature product classification program available from the inventor, however any other classification strategy may be employed as well.

Referring to FIGS. 1 and 2, it may be seen that FIG. 1 is a cross section through one object conveying lane, while FIG. 2 depicts a four lane machine configuration. From the cross sections in FIGS. 3 and 4, it may be seen that each pair of inverter wheels (11) are mounted and rigidly attached to a common shaft (33), forming an independent self contained unit. Although it is possible to build a single lane machine, or machines with odd lane numbers, it is recommended that the minimal number of lanes per machine should be two, while additional lanes may be added in pairs as required. The preferred embodiment examplified in FIG. 4 shows two chain wheels on each inverter wheel, whereby each cup or tray lane runs between two chains. However more economical configurations are also possible, wherein two cup or tray lanes are supported by three or even two chains only, while using three or two chain wheels per two lanes respectively, in the upper or lower conveyors (3) and (18).

The object throughput limit per lane, is determined by the linear speed of the cup-conveyors (3) and the number of grippers (9) on the inverter wheel (11). Another limiting factor may be software execution time per inspected object, which tends to increase proportionally with the number classification features. Since the data acquisition at the inspection stations is performed serially it is not detrimental in limiting throughput.

For fresh produce sorting, eight grippers per wheel as shown in FIG. 3 seems to be optimal, however more or less grippers per inverter wheel may be similarly implemented for other product types if required.

Commercially available automatic weight sizing machines for fresh produce, utilizing cup-conveyors similar to (3), employ throughputs of up to about four cups per second. Considering new advances in high speed computing hardware and software, similar throughputs may be attained in the multiple sensor machine, utilizing an eight gripper inverter wheel (11), as shown in FIG. 3.

For sensor evaluations and calibrations as well as determination of the actual classification efficiency, by the various product features, the machine disclosed hereby is equipped with classified products sampling stations (23), as shown in FIG. 2.

In the configuration examplified in FIG. 2, the product may be classified into 12 categories at most, as determined by the number of side delivery conveyors (17)

for carrying the classified products to the packing stations. More than one side delivery conveyor (17) may be employed for any particular grade, if required to accomodate its quantitative predominance in the raw material entering the machine on the conveyor belt (1). Apart from total machine length, there is no restriction on the number of side delivery conveyors (17), which may be used for a given product classification task.

When it is desired to draw a sample of products classified by the machine, the drive motor of the side delivery conveyors (17) is stopped momentarily and reversed as shown by the bottom arrows line in FIG. 2. This diverts the products to the sampling bins (23), rather than in the normal direction to the packing stations. In the hypothetical configuration of FIG. 2, the first three bins (19) may represent three sizes of grade C, the next four bins (20), four sizes of grade B and the last five bins (21), five consecutive sizes of grade A fruits. Once a sufficient amount of fruits is accumulated in the bins for statistically significant sample sizes, the above belt drive motor is reversed again and normal product distribution is resumed.

The sampled products may then be closely examined manually by expert inspectors, measuring all the classification features of each product, according to a preset scale, while feeding the data into the master microcomputer, by a remote console stationed at the sampling bins, (not shown in FIG. 2). A computer program, may then be implemented to process this data. The output of this proram may be utilized in several ways:

a. Evaluation of new sensors, as to the feasibility of measuring different product features.

b. Calibration of sensors and product classification scales.

c. Comparing machine product classification to manual precise classification by an expert inspector.

d. Quality control checks by federal or other agents if required.

e. Determination of actual feature scale probability densities, as required for implementation of Bayesian type decision making algorithms.

Once the manual product inspection is completed, the products in the sampling bins (23) may be released onto the sampled products return conveyor belt (22) and returned to the raw material conveyor belt (1) via the sampled products return roller conveyor (24).

In summary note that although the above machine configuration and operating cycle was described for sizing and grading fresh produce, only marginal modifications are required to adapt it for inspection and classification of other items, such as processed food products, avionics components, industrial products or small electronics components, integrated circuit boards and chips, radioactive ore etc.

For large products the cup-conveyors (3) and (18) may be made larger while the cups (15) may be substituted by suitably shaped large trays to fit the contour of the product. Similarly for tiny items, the whole machine and cup-conveyors may be miniaturized. Conveying speeds may also be decreased or increased, or an intermittent stop-and-go conveying mode may be implemented as appropriate to the products and inspection task at hand. In all cases the same principles of the double conveyor and inverter wheel augmented by suitable product grippers applies.

2. Object Grippers and Associated Sensors

Figure 10:
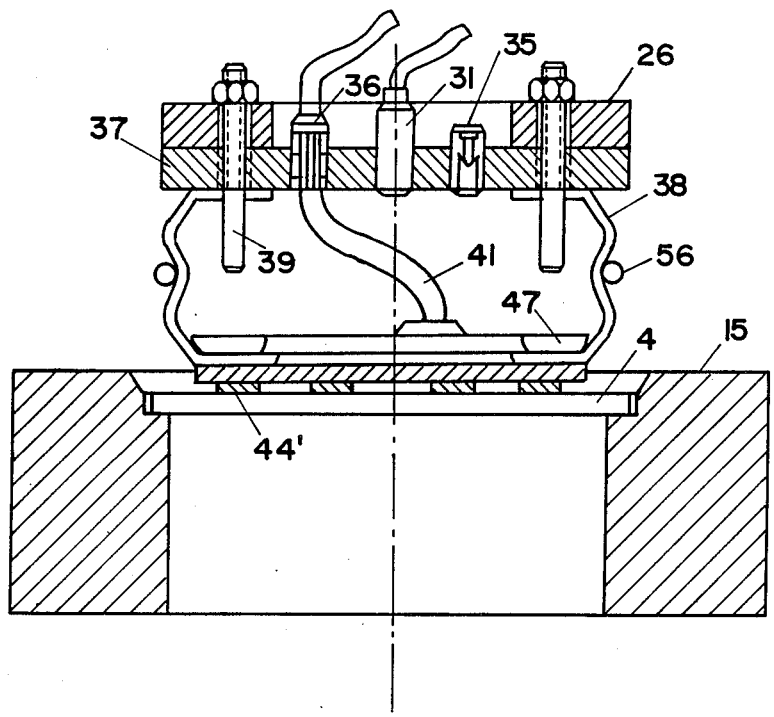
FIG. 10 Shows cross section of tray and semiflexible gripper, suitable for inspection of disc or plate shaped products, such as can or bottle closures, compact discs or printed circuit boards. Here the gripper is outfitted with a probe connector that engages selected leads or junctions on the board, for conducting electrical functionality checks.

The embodiment of the invention permits adapting the grippers and cups or trays, to suit inspections of a wide range of product classes. Thus FIGS. 5, 6 and 13, depict three possible cup-gripper configurations for inspecting spherical, spheroidal or horizontally placed cylindrical objects. The tray-gripper configurations in FIG. 7 and FIG. 8, may be used for inspecting parallelepiped shaped and upright cylindrical objects, or thick discs. Similarly the cup-gripper configuration in FIG. 9 depicts inspection of an amorphous object, while the tray and semi-flexible gripper configuration in FIG. 10 shows a typical arrangement for inspecting plate shaped objects, such as printed circuit boards.

With reference to FIG. 1 note that identically shaped cups or trays (15) in both the upper and lower conveyors (3) and (18) may be employed for inspecting substantially symmetrical objects such as examplified in FIGS. 5, 6, 8, 9 and 10. Differently shaped cups or trays are required in the upper and lower conveyors, when the shape of the upper side of the product is substantially different from its under side, as examplified in FIG. 7.

Apart from retaining the products in the cups during the inversion process, the grippers (9) may simultaneously measure various mechanical properties thereof, as well as provide a means for conducting automated electrical functionality diagnostics of the inspected product. To this end, the gripper pad contacting the inspected object may be rigid or flexible. Also the gripper body attached to the gripper arm (26) or (26'), may be essentially rigid or flexible. Thus the grippers in FIGS. 5, 7, 9 and 10 comprise flexible bodies in the form of air-tight rubber bellows boots (38), which may be outfitted with flexible gripper pads in the form of a diaphragm (44), as in FIGS. 5, 7 and 9, or with rigid gripper pads (44') as in FIG. 10. On the other hand, the grippers shown in FIGS. 6 and 8 comprise a rigid body (51) and thin rubber pad attached thereon. Flexible pads, made of resilient materials may be similarly attached to the rigid gripper body (51) if required. The rigid gripper body (51) may incorporate a load cell for measuring the gripping force, or a tactile sensor pad (52) may be employed as shown in FIG. 6. The rigid gripper version in FIGS. 6 and 8 is most useful when it is desired to obtain accurate quasi-static force-deflection characteristics of the inspected product, in order to assess its mean stiffness, e.g. firmness or ripeness of fruits, stiffness of engine mounts, elastomers etc. The flexible finger gripper in FIG. 13 utilizes a leaf spring (44'') for directly engaging the product (4).

In all gripper configurations the movement of the gripper arm (26) or (26') is constantly measured by an optical shaft encoder which is an integral part of the stepper motor (25). In configurations such as in FIG. 6 or 8 the zero deflection e.g. the initial undeformed size of the product is detected by the load cell or tactile sensor when the pad first contacts the product. The initial sudden increase in the load cell output also signals the stepper motor (5) to reduce the approach speed, while force deformation data collection begins and continues until a preset maximal gripping force is attained. The removal of the load on the product (4) in the cup (15) begins as it reaches the bottom of the inverter wheel (11), as signalled by the optical encoder in the synchro motor driving the inverter wheel shaft (33) in FIG. 4. Note that the initial reading of the optical encoder in the stepper motor (25), may be used to measure the vertical dimension, i.e. the thickness of the product (4). In conjunction with the horizontal dimensions obtained by optical means at the reflected radiation inspection station (5) and the cup weighing station (14) in FIG. 1., this enables accurate computation of product volume and its specific gravity. In many products specific gravity is an indicator of internal quality, especially when it is determined by liquids to solids ratios. Using specific gravity as a classification feature for some fresh produce cultivars, may enable separation of freeze damaged fruit from sound fruit, thick skinned fruit from thin rind fruits, ripe and high juice content fruit from immature fruit, dehydrated from moist foods etc.

For an eight inspection stations inverter wheel, such as (11) in FIG. 3, and a speed of 4 cups per second, the entire force application and removal cycle lasts about 1 second. For a given throughput speed, longer cycle times may be obtained with larger inverter wheels incorporating more than eight inspection stations on their periphery.

When in addition to force-deflection, it is also desired to obtain information about the contact surface characteristics and pressure distribution thereon, a tactile sensor may be employed in place of the load cell. In this case the first contact point between the gripper pad and the product is detected by the tactile sensor, which can also measure the contact area shape, contour and pressure distribution over it. The shape and size of the contact surface between the product (4) and the tactile sensor (52) depends on the approach of the gripper arm (26), as well as on the size, shape and stiffness of the product (4). For a given gripper approach and product size and shape, the contact surface is proportional to its firmness or rigidity. Hence the tactile sensor may be viewed as a "mechanical thumb", as its operation is similar to pressing a thumb to the product and assessing its formness by the indented surface contact area of the fingers, while applying a given force or pressure.

The flexible gripper (9) as depicted in configuration in FIGS. 3 and 4 is somewhat less accurate when measuring force-deflection, however it also affords measuring mechanical product properties by dynamic loading, e.g. measuring its vibration response characteristics simultaneously with force deflection.

The flexible gripper bodies exemplified in FIGS. 5, 7 and 9 comprise a base plate (37), bolted to a gripper arm (26) by stud bolts (39). A rubber bellows boot (38) is bonded to the metal base plate (37), forming an air tight seal. The other end of the boot (38) is also sealed airtight by a double layer rubber diaphragm (45), bonded to the rubber boot periphery, forming a flexible gripper pad (44). A metal retaining ring (47), bonded to the inside edge of the rubber boot, and boot ring (56), retain its basic shape and active dimensions, even when the gripper (9) is loaded excentrically due to irregularly shaped products. The initial degree of rigidity of the rubber boot (38) and the gripper pad (44) is controlled by a pre-charge air pressure introduced into the air tight boot (38) through the inlet pressure valve (35). Sometimes there may be no need for a precharge pressure, i.e. the initial pressure in the boot is equal to the ambient atmospheric pressure. In any case, a pressure transducer (31) constantly monitors the air pressure in the boot (38). This pressure varies as the boot (38) is compressed or released, however barring air leaks the pre-charge pressure, when the boot is unloaded externally remains fairly constant. It follows then that the air pressure in the boot (38) as measured by the pressure transducer (31) and applied to the gripper pad (44), is also equal to the pressure applied to the gripped product (4).

As the gripper arm (26) and boot (38) approach the product (4) retained in the cup (15) the gripper pad (44) is kept approximately flat because the pre-charge pressure is only slightly higher than the ambient pressure. Initially there is just one contact point between the gripper pad (44) and the product (4). At this point the reading of the encoder in the stepper motor (25) may be used for measuring the vertical product dimension, similarly to the rigid gripper configuration described above. With further approach of the gripper arm (26) rotated by the stepper motor (25), using the pressure transducer signal (31) for closed loop feedback control, the gripper pad (44) begins to flex inwards as it conforms to the shape of the gripped product (4). A flexible strain gauge (46) embedded between and bonded to the two rubber layers of the gripper pad (44) generates an electrical signal, which is proportional to its flexure. The relatively weak signal of the strain gauge (46) in the flexible gripper pad (44) is transmitted by the leads (40) and the air tight lead connecting plug (36) to the conditioning and amplification electronics (54) FIGS. 3 and 4. The amplified signal is then transmitted to the slave microcomputer (32) on the inverter wheel (11) for further processing by appropriate product classification software.

Instead of a flexible gripper pad (44), as in the flexible grippers of FIGS. 5, 7 and 9, most suitable for engaging convex objects, the semi-flexible gripper configuration in FIG. 10, employs a rigid gripper pad (44'). This pad is better suitable for inspecting plate shaped objects, such as printed circuit boards. Male of a non conducting material, it incorporates a set of bulges projecting from its surface, interspaced with a set of probe connectors, which engage selected sites on the printed circuit board (4). The projecting bulges retain the board (4) in the tray (15) by engaging blank sites on the board, while the probe connectors establish electrical contacts at selected junctions or leads of the circuit. Thus, a functionality check may be performed, in conjunction with visual inspection. Power supply to the board and the signals from it are transmitted via leads (41) and air tight connecting plug (36). These signals are sent to the slave microcomputer (32) on the inverter wheel (11) for processing by appropriate product classification software. Thus, the shape of the pad, probe connectors set and associated pattern of bulges, are unique for a specified circuit board.

The four gripper connecting studs (39) protrude down into the rubber bellows boot (38). This limits the contraction of the boot (38) whenever the retaining ring (47) contacts the ends of the studs (39). This should not happen in normal operation due to the naturally increasing pressure within the boot as it contracts. However should a puncture occur, this safety feature prevents the boot from collapsing.

In FIGS. 5, 7, 9 and 13, the product (4) is seen to be supported by the vibration actuator head (42), which may be incorporated when it is desired to measure the mechanical properties of the product by dynamic loading. The vibration actuators (10) may be dismantled if it is not desired to use product vibration response as a classification feature. In this case the products (4) would rest in the cups or trays (15) directly as shown in FIGS. 6, 8 and 10.

When vibration response is included as a product classification feature, the vibration actuator head (42) automatically enters through the opening in the cup (15) rising the product (4) slightly off the supporting surface of the cup, while the flexible gripper pad (44), or leaf spring (44″), begins to apply pressure to it. In this configuration the first contact between the flexible gripper and the product is detected by the strain gauges (46) or (46′), as soon as the gripper pad (44) begins to deform. This triggers the approach speed reduction of the stepper motor (25) and beginning of pressure deflection data acquisition, similarly to the rigid gripper configuration described above. However since the gripper is not rigid, its deformation must be subtracted from the deformation measured by the optical encoder of the stepper motor (25). The flexure of the strain gauges (46) and (46′) is proportional to the deformation of the gripper. Thus the signal it emits, while compressing the product, may be used in conjunction with the signal from the optical encoder, to quantify product deformation. With careful calibration the deformation measurement accuracy obtained by this method should be only slightly lower than in the rigid gripper configuration. Also rather than force deformation, the signals obtained here are mean pressure versus product deformation. For some products, e.g. fruits and vegetables, measuring pressure directly is more meaningful than force. Nevertheless if the contact area and the pressure distribution over it are known, both the mean pressure and the total gripping force may be computed, but this takes up additional computer time.

Each of the vibrator assemblies exemplified in FIGS. 5, 7 and 9 comprise two vibration actuators. The lower vibrator (10), is an electromagnetic vibration actuator for generating frequencies in the 10 Hz to 20 KHz range, while the upper vibrator (43) is a piezoelectric actuator for generating ultrasound frequencies in the range of 20 to 60 KHz. Either one of them may be driven separately or they can operate in tandem, while each excites a different component of the inspected product.

The vibration input energy to the product (4) by the vibration actuator head (42) is monitored by the lower acceleration transducer (34′) while the corresponding output acceleration is measured by the upper acceleration transducer (34). The signals from both transducers are fed through the leads (41) to the conditioning and amplification electronics package (53), and then to the relative displacement, power and energy dissipation measurement system (55) in FIG. 3. The operation of this system is summarized by the block diagram in FIG. 11, as described below.

Note that the dual vibration actuator configuration is needed only in special cases, when the product must be excited by a very wide frequency range, e.g. 10 Hz to 60 KHz, which most inspections will not require. Thus, in most cases only the lower actuator (10), or the upper actuator (43) will be required, wherein the actuator head (42), is bolted directly to either one of said actuators, while using an appropriately thicker base plate (49).

The flexible gripper and its sensors in conjunction with the vibration actuators, comprise a sophisticated system, whereby most versatile measurement of mechanical product properties can be accomplished "on the go". These may be carried out while the conveying system moves at a constant speed, or during stop intervals, when it intermittently moves and stops by a preprogrammed stop-and-go conveyor motion. The modular construction enables usage of only part of its features, or all of them simultaneously. It is particularly suitable for delicate handling and inspection of visco-elastic objects, e.g. most fruits and vegetables, food products and industrially manufactured appliances and components.

The different possibilities of product inspection and classification by mechanical properties, utilizing either the rigid or the flexible gripper configurations and sensors, may be summarized as follows:

a. Overall product stiffness via force or pressure versus deformation characteristics. Most suitable for measuring visco-elastic and visco-plastic properties of products, e.g. fruits, vegetables, food products, engine mounts, expanded polymer products or foams etc. In the rigid gripper, configurations as in FIGS. 6 and 8, the gripper force is measured directly by a load cell in the gripper body (51), while the deformation is recorded by an optical encoder in the stepper motor (25) in FIG. 4. In flexible gripper configurations in FIGS. 5, 7 and 9 the gripper pad pressure is measured directly by a pressure transducer (31), while deformation measurement is accomplished by subtracting the strain gauge signals from the said encoder signal.

b. Product indentation characteristics, i.e. "Mechanical Thumb", via contact surface contour and its contact area, pressure distribution, center of gravity and direction of centroidal axis. Integration of the pressure over the contact surface are also permits computation of the total gripping force.

Rigid gripper configurations may use a tactile sensor in place of a force load cell. Overall product stiffness may be obtained simultaneously as well.

c. Ultrasound energy transmission for detecting voids, cracks or similar internal product discontinuities. May also be used for measuring water or moisture content in the product.

d. Automated vibration inspection, enabling measurement of frequency response and internal damping characteristics via dynamic relative displacement, power and energy dissipation measurement system, as summarized by the block diagram in FIG. 11. These classification features are most suitable for inspecting large quantities of industrial, avionic or military systems incorporating mechanical and electronic components, which must comply with dynamic loading specifications such as ASTM standards or MIL-SPEC's. Vibration energy dissipation may also quantify mechanical properties of fruits, vegetables and processed foods.

Once a preset gripper pressure is applied to the product, the vibration actuator (10) in FIGS. 3. and 4 may apply any desired vibration profile as the product (4) in the cup (15) moves around on the inverter wheel. The dwelling time of the vibration test may be very short, say a 0.5–0.75 sec. burst for high speed produce sorting, or it may last several minutes when a relatively slow frequency sweep is required for automatically generating and recording a Bode diagram test record for each product.

Different vibration profiles may be chosen, via the settings of the function generator driving the electromagnetic vibration actuators (10).

For generating constant input acceleration level frequency sweeps, such as needed for recording Bode diagrams, acceleration transducer (31) monitors the output, while transducer (31′) serves for controlling the input by closed loop feedback to the function generator. Dwelling at selected narrow band random frequencies or at selected discrete frequencies, corresponding to product resonance bands may be similarly accomplished.

For high speed automatic vibration inspection, e.g. fruits and vegetables or processed food products etc. a white or pink noise driving signal may be used. Short vibration bursts followed by high speed FFT processing, affords identification of response peaks and low frequency response bands corresponding to distinct product properties, which may serve as classification features.

Figure 11:
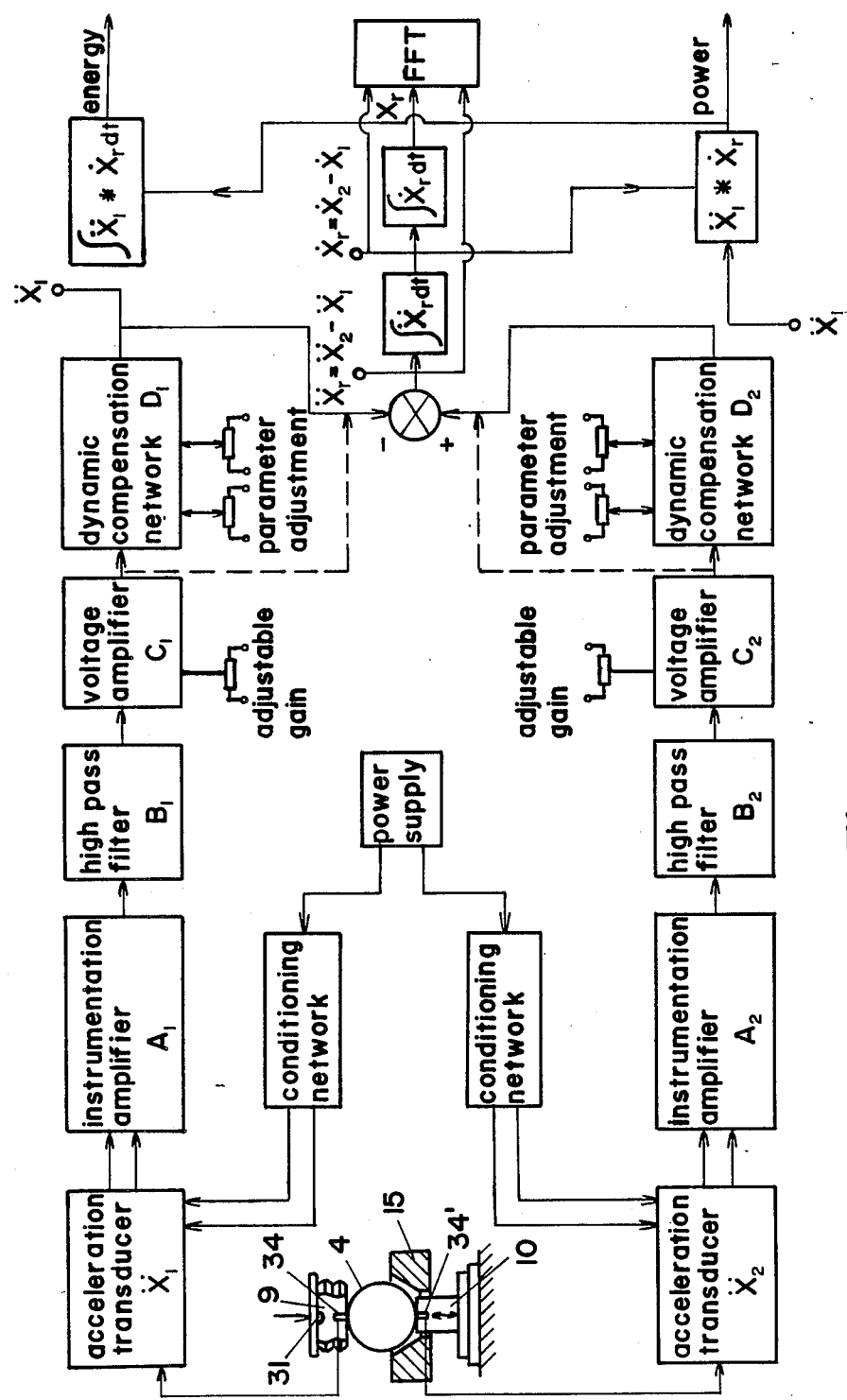
FIG. 11 Shows block diagram of relative displacement, power and energy dissipation measurement system.

Regardless of the vibration profile employed, additional information may be extracted from the acceleration transducer signals (34) and (34'), by the relative displacement power and energy dissipation measurement system summarized by the block diagram in FIG. 11. After suitable amplification and low pass filtering each signal is passed through a dynamic compensation network, which matches the gain and phase characteristics of the two acceleration transducers, and extends their usable frequency band. This affords precise derivation of the relative acceleration between the top and the bottom of the product. The dynamic compensation network is necessary since no two acceleration transducers of the same make are exactly alike. Without compensation, part of the relative acceleration signal may be due to the difference between the transducers rather than between the input and output accelerations. After the compensation, two real time consecutive integrations of the relative acceleration yield the relative velocity and displacement respectively. Then the product of the output acceleration by the relative velocity and its integral give the power and energy dissipated in the product, due to the input vibration burst. This energy is a direct measure of the internal damping properties of the product, which may be used as a product classification feature.

Apart from the energy dissipation, the three additional signals thus created, i.e. the relative acceleration, velocity and displacement are more effective for identifying tell tale low and high response frequencies, than the usual output to input acceleration ratio employed in conventional vibration testing. Firstly because the relative acceleration derived from the compensation network is by far more precise in quantifying the frequency response of the product. Secondly a greater dynamic range is afforded for a given frequency band. To see this observe that at the low frequency end, relatively large amplitudes may be present in the spectrum while the associated accelerations may be very low. Conversely at the high frequency end of the spectrum large acceleration peaks may correspond to negligibly small amplitudes. Similarly in the mid-range of the spectrum, velocity peaks dominate both the corresponding accelerations and displacement amplitudes. Since this classification feature hinges on spectral differences of product categories, it is more useful to use the relative displacement signal for FFT processing, when the differences between the spectra are most predominant in the low frequency range. Similarly the differential velocity or acceleration should be used when the spectral differences are predominantly in the mid and high end of the spectrum respectively.

In order to avoid the need for switching between the different spectra, a composite signal is derived by summing the three signals together prior to FFT processing, as depicted on the right side of FIG. 11. The significantly larger dynamic range of the composite spectrum thus derived, in comparison the spectra of the three components, affords superior product classifications by spectral differentials in the entire frequency band.

It should be noted that the modular structure of the mechanical properties inspection stations as described above, permit simultaneous classification by product stiffness, ultrasound energy transmission, vibration response spectral differentials and differences in energy dissipation i.e. vibration damping characteristics. Any one of these may be disregarded or switched off whenever inappropriate to a particular product classification task.

3. Computing Hardware Sensors and Actuators

The computing hardware, sensors and actuators and associated software, are summarized by the block diagram in FIG. 12. The flow of information between the different units is shown by the arrows. This hardware comprises three interconnected microcomputer systems and associated peripherals, marked in the block diagram of FIG. 12 by one, two and three asterisks respectively.

The master microcomputer (*) serves three main purposes. Firstly it comprises the operator's interface for machine parameter settings, long term statistical data acquisition and storage on disc, as well as book keeping and printing hard copy reports if required. Its second main task is receiving data samples from stationary slave microcomputer (**), and sending back updated lookup tables of optimal product classification feature scales. These periodically obtained data samples represent the most recent "raw material composition" e.g. mean grade proportions in the inflowing stream of objects, and the associated most recent classification decision profile. The purpose of this process is to minimize product classification errors, under variable raw material composition, while executing a given product classification policy, as may be implemented by a special algorithm developed by the inventor but not described herein.

In addition to the above two main tasks, the master microcomputer may also be used for running various off line programs. One example of these may be a management decision aid program, comprising an expert system for guiding the operator in choosing optimal product classification policies, in a given market environment. Another such program may be run in conjunction with the classified products sampling stations. Using data keyed in by expert inspectors, as they reclassify the sample products, this program enables precise sensor calibrations and checkups of actual classification efficiency of the machine.

The stationary slave microcomputer () controls the cup drop triggers, sending the classified products onto the appropriate side delivery conveyors (17) in FIGS. 1 and 2, while running the main product classification program, which is unique for each inspection task. It is also responsible for data acquisition and processing, from the sensors of the stationary product inspection stations, (5), (6), (7), (14) and (8) in FIG. 1. Additional data is received from block (*), i.e. from the revolving slave microcomputer (32), via the slip ring assembly (27) in FIG. 4. This data is derived from the sensors (31), (34), (34'), (46), (52), 44' as examplified in FIGS. 6 and 10 and optical encoders in the stepper motors (25) in FIG. 4.

After processing the sensor data, the product classification program compares it to the classification scale lookup tables, whereby a decision is made as to the category of the inspected product. As the products are inspected and classified in turn, raw material composition and decision profile data may be continuously accumulated and periodically sent to the master microcomputer, while newly computed updated lookup tables are received from it.

Each inverter wheel (11) in FIG. 3 incorporates one revolving slave microcomputer (32), marked by block (***) in FIG. 12. Thus a four lane machine, as depicted in FIG. 2 requires one master microcomputer (*), one stationary slave microcomputer () and four revolving slave microcomputers (*) on the inverter wheels. This configuration allows parallel processing wherein the slave microcomputers are dedicated for data acquisition and real time product inspection and classification only, while the master microcomputer (*) is saddled with most of the number crunching tasks off line.

In addition to data acquisition from the revolving inspection stations sensors, the said slave microcomputers (32), also control the gripper stepper motors, i.e. the motion of the gripper arms (26) in FIG. 4. They are also responsible for activating and deactivating the vibration actuators (10) and (43) in FIGS. 5, 7 and 9. If an electrical functionality check is implemented on the inspected products, they must also run an appropriate diagnostics program.

The slip ring assemblies (27) in FIG. 4, comprise the communication links between the revolving slave microcomputers (*) and the stationary slave microcomputer (), which in turn communicates with the master microcomputer. The said slip ring assemblies (27) are also used for transferring power to the revolving slave microcomputers (32), the signal conditioning and amplification electronics (53) and (54), the relative displacement power and energy dissipation measurement system (55) in FIG. 3 and the vibration actuators (43) and (10) in FIGS. 5, 7 and 9. This affords cool operation and compact light weight construction of the revolving microcomputers and electronics, since heat generating and heavy transformers or bulky AC to DC converters are not carried on the inverter wheels. Also, only one function generator and power amplifier is required for driving all the vibration actuators (43) and (10) in FIGS. 5, 7 and 9 while switching control logic is software implemented by the autonomous slave microcomputers (32) mounted on each inverter wheel, as shown in FIGS. 3 and 4.

All computing hardware and peripherals may be implemented by standard stock items, readily available from different vendors at competitive prices. According to the computation functions summarized in the block diagram in FIG. 12, the following guidelines are given as regards computer suitability:

The functions of the master microcomputer (*) may be implemented by a low cost personal microcomputer, incorporating a mouse user interface, multi-tasking processing, fast color graphics and standard digital I/O.

For a two lane, relatively slow speed inspection machine the functions of the stationary slave microcomputer (**) may be performed by a high end personal microcomputer, via multi-channel digital I/O, A/D, D/A, frame grabbing boards, extra memory buffers and accompanying software. To perform these functions in a four lane or larger machine, operating at high speed, a more powerful industrial microcomputer would be required. Currently available machines are capable of high speed 512×512 or 1024×1024 pixels image acquisition at 8 bit resolution and processing in essentially real time.

The revolving slave microcomputers (***) mounted on the inverter wheels, are essentially single board microcomputers incorporating digital and analog I/O.

In FIGS. 3 and 4 they are schematically depicted as STD BUS cages (32), including both the microcomputer and I/O boards. Such low cost compact units are manufactured by many different companies, targeted for various industrial control applications. Recent developments in "On a chip" microcomputers may enable implementation of these functions in yet a more compact and very low cost package.

4. Optimal Product Classification Software

It is tacitly assumed that most of the features X, of the products to be inspected and used for classification by the present invention, can be measured by different sensors and quantified by suitable feature scales YX, where Y expresses the degree or "strength" of each feature X. Examples of such scales may be product weight, dimensions, firmness, color, internal and external defects and blemishes etc. Or in case of functionality checks, a binary 0 or 1 index may be used, to quantify numerically the result of the inspection. The scales of some features, such as weight or dimensions are self evident, while the scales of other features must be predetermined by an expert inspector, to correlate the sensor reading to the feature strength, as provided for by the automatic product sampling means i.e. items (17) and (19) through (24) in FIG. 2.

Interpretation of digitized images acquired form the reflected and or transmitted radiation sensors, may be performed by well known digital image processing techniques. To this end, software packages for "Pattern recognition" and for "Image understanding" are commercially available.

In some cases the sensor readings uniquely classify the feature with absolute certainty, especially when the feature scale distribution may be considered to be binary, i.e. the feature is either detected or not. Inspection of printed circuits for lead continuity is a good example of such a feature. In this case, once a lead break is detected the decision making process for product classification is trivial.

In most cases the feature scale within a product category follows a continuous distribution, and can usually be approximated by the normal (Gaussian) distribution. Bayesian type algorithms may be implemented to address this more difficult classification problem, i.e. when the sensor readings and associated interpretation software, can provide only a classification probability, rather than uniquely classify the product.

.Consider for example the classification process of sorting lemons into a yellow and green category. Here the amount of chlorophyl in the rind indicates the degree of "greenness" while its absence determines the degree of "yellowness". Using a pair of sensors for measuring this feature scale, i.e. yellow to green light reflectance ratio, will leave some "slightly yellow" in the green category, while "slightly green" lemons will be classified as yellow category. A classification policy must be adopted whereby a "scale separation line" divides the two lemon categories, according to some industry standard or policy based on marketing considerations. Clearly in this case the feature scale is continuously distributed within the product categories. In statistical terms we may say that there is an overlap between the probability density curves of the feature scales of these two categories, quantifying the probability of misclassifications about a predetermined separation line. It may be shown that the extent of this overlap depends on the average yellow/green ratio of lemons in the raw material as well as on the feature scale probability density curves within the categories. If, as in this example, the composition of the raw material is not constant, an adaptive decision algorithm is required to minimize product misclassifications at all times. To this end, a software package, which is not a part of the present invention, may be obtained from the inventor. This software package, comprises a general machine learning, optimal product classification algorithm which is readily adaptable, for various computerized inspection tasks, that can be implemented by the machine disclosed herein. In conjunction with the hardware, this algorithm provides a means of continuous statistical sampling of the raw material as well as each classification scale distribution. Information from on line statistical analysis of these samples, is used for automatic readjustment of classification scales for minimal probability of product misclassifications. Basically this means that the machine constantly checks the composition of the raw material inflow, while analyzing its previous decisions pattern in terms of classification errors it made, wherewith it automatically readjusts its sorting strategy to improve classification accuracy. The data derived in the sampling process may also be used for computing a set of weighted mean classification efficiency indexes, for each product classification feature. These indexes quantify the accuracy of the machine, i.e. they provide assessment of the machine's performance with respect to the said optimal product classification policy, or prevailing industry standards.

As the structure of these programs will vary from product to product, and since they are not an integral part of the present invention, their structure will not be described here in detail.

I claim:

1. A method of automatically inspecting, classifying, sorting and grading discrete objects of different product classes in accordance with their distinctive features and properties, by successively examining both sides of each said object, comprising
    automatically loading each said object into a cup or tray of a first chain conveyor, causing said object to be moved by said first conveyor to pass sensor means for transmitting to computer means signals relating to selected features, properties or functionality of each said object, as sensed on one side of each said object,
    causing each said object to be transferred from its respective cup or tray at the output end of said first conveyor into a cup or tray of a second chain conveyor running underneath said first conveyor, by means of gripping means for retaining each said object in its cup or tray during its downward movement around a set of chain wheels supporting the output end of said first conveyor and to release each said object in reversed position into a respective cup or tray of said second conveyor,
    causing each said object to be moved by said second conveyor to pass second sensor means for transmitting to said computer means signals relating to the features, properties or functionality of said object as sensed on its other side, and
    causing said computer means to issue signals to discharge means arranged along said second conveyor to effect removal of said objects from said cups or trays into consecutive collecting stations positioned along said second conveyor, in accordance with the sensed features and properties.

2. An apparatus for automatically inspecting, classifying, sorting and grading discrete objects of different product classes in accordance with their distinctive features and properties, by successively examining both sides of each said object, comprising,
    a first, upper chain conveyor running between a front set of chain wheels and a rear set of chain wheels, containing at least one longitudinal lane of equidistantly spaced cups or trays each shaped to hold one object of a particular product class,
    a loading station for positioning one said object into one said cup or tray,
    a second, lower chain conveyor running underneath said first conveyor in parallel and spaced relationship, in synchronized manner but in opposite sense of direction, and containing at least one lane of equidistantly spaced cups or trays each shaped to hold one object of said particular product class,
    a transfer station at the rear end of said first conveyor comprising a plurality of gripper units rotating at the rotational speed of said rear set of chain wheels for retaining each object in its cup or tray during its downward travel around said chain wheels and to gently release it into a corresponding cup or tray of said second conveyor,
    discharge means positioned along said second conveyor for discharging each object out of its cup or tray into one of a plurality of consecutively arranged collecting stations each destined to hold or convey all objects of same or similar features and properties,
    sensor means positioned along said first and said second conveyor for sensing the features and properties of each said object on the first side facing the respective sensors positioned along said first conveyor, and on the opposite side facing the respective sensors positioned along said second conveyor, and to transmit to computer means signals relating to the position of each said object on said conveyors and to the features and properties or functionality according to which said objects are to be classified,
    computer means for transmitting signals to said discharge means with regard to each object, effecting said discharge means to discharge object out of its cup or tray into its appropriate collecting station in accordance with a predetermined combination of the sensed features and properties.

3. Apparatus of claim 2, further, wherein said first and second conveyors each comprise several parallel lanes of a plurality of equidistant cups or trays whereof each two adjoining lanes are supported by at least two conveyor chains, said chains being supported by a set of at least two chainwheels at said loading station and by a set of at least two "inverter" chain wheels at said transfer station, each set of chainwheels being rigidly mounted on a common shaft and rotated at identical rotational speed.

4. Apparatus of claim 3, comprising several gripper units mounted on one side of said set of inverter chainwheels, each gripper unit consisting of a gripper body and pad or leaf-spring, positioned above and corresponding to said cup or tray during its motion along the circumference of said inverter wheels and connected by an arm to an actuator for moving said pad or leaf-spring into contact with one said object, held in said cup or tray while said cup or tray passes the top of said inverter wheels and to hold said object in said cup during its passage around said inverter wheels into its bottom position, and to remove said pad or leaf-spring from said object in this bottom position, permitting said object to slide or drop into a cup or tray of said second conveyer.

5. Apparatus of claim 4, comprising one actuator for each gripper unit in the form of computer-controlled electric stepper motor incorporating a shaft encoder attached to said inverter wheels and connected to said gripper body by an arm.

6. Apparatus of claim 4, further, wherein said gripper bodies are flexible and further comprising pads for conforming to the shape of said objects and provided with pressure sensors for measuring and controlling the pressure exerted by said actuators through said pads on said objects, in order to prevent damage to these objects, as well as effecting measurement and classification of each object by means of the pressure-deformation characteristics or firmness of each said object.

7. Apparatus of claim 4, wherein said gripper bodies are rigid and further comprising pads, each provided with a force-load cell for measuring and controlling the force exerted on objects by said grippers and to classify objects, such as fruit, in accordance with their firmness and force-deformation characteristics.

8. Apparatus of claim 4 comprising flexible gripper units in the form of a leaf-spring, connected by an arm to an actuator for moving said leaf-spring into contact with one said object, held in said cup or tray, provided with strain gauges for measuring and controlling the force exerted by said actuator through said leaf-spring in order to prevent damage to said object, and a response acceleration transducer for measuring the output acceleration of said vibrationally excited object in order to classify said object by vibration response characteristics or by its firmness.

9. Apparatus of claim 4, wherein said pads are rigid and said gripper bodies are flexible, further wherein said pads are in the form of rigid non-conductive plates provided with electrical probe conductors for engaging with conductors on the inspected object, such as a printed circuit, for the purpose of analysing electrical functionality.

10. Apparatus of claim 4, further comprising one vibration actuator each mounted on said inverter chainwheel set opposite each gripper unit, incorporating vibration sensing means to effect controlled vibration profiles to inspected objects, and further comprising a flexible resilient gripper pad or leaf-spring above each cup or tray, each pad or leaf-spring containing response vibration sensing means to effect measurement of vibrational response of each said object.

11. Apparatus of claim 10, wherein excitation and response acceleration transducers are incorporated respectively in each said actuators and said flexible gripper pad or leaf-spring, for the purpose of sensing input acceleration applied to one side of an inspected object, and the output acceleration on the other side of said object, as well as the difference between said input and said output acceleration.

12. Apparatus of claim 11, further wherein conditioning, amplification and signal processing electronics, interfaced to said excitation and response acceleration transducers, are positioned on said inverter chainwheel, for the purpose of measuring firmness, frequency response, relative displacement, power and energy dissipation of said inspected objects.

13. Apparatus of claim 2, wherein said cups or trays, have a prismatic recess inner surface, for holding horizontally placed objects of cylindrical shape, such as cans, shells, bullets and objects of similar shape.

14. Apparatus of claim 2, wherein said cups or trays, have a retangular recess inner surface, for holding objects of substantially parallelepiped shape, such as boxes, cartons, containers, and objects of similar shape.

15. Apparatus of claim 2, wherein said cups or trays are provided with an opening in their bottom protions for the purpose of examining objects by penetrating radiation sources such as emitting X-rays, Y-rays, or lasers, positioned above or below said lanes of cups or trays, and corresponding radiation sensors positioned respectively below or above said lanes of cups or trays.

16. Apparatus of claim 2, wherein said cups or trays are provided with an opening in their bottom portions for the purpose of exciting and examining each object by vibration actuators.

17. Apparatus of claim 2, wherein said cups or trays are of a configuration permitting their slidingly passing over a load cell bridge.

18. Apparatus of claim 2, wherein said first and said second conveyor progress at identical, constant velocity, but in opposite sense of direction, in a continuous motion, for the purpose of examining each said object on-the-go.

19. Apparatus of claim 2, wherein said first and said second conveyor progress at identical velocity, but in opposite sense of direction, in a stop-and-go intermittent motion, for the purpose of examining each said object in a stationary position.

20. Apparatus of claim 2, wherein said sensor means comprises reflected radiation sources positioned above said lanes of cups or trays of said first and said second conveyor such as white light, ultraviolet or infrared light and radiation detecting and image acquisition devices, such as vidicon or CCD-cameras, or light sensors, positioned above said first and said second conveyor, in the vicinity of said radiation sources.

21. Apparatus of claim 2, further wherein said second, lower conveyor's cups or trays pivotally attached to said conveyor chains and held in horizontal, object-holding position by retaining means, said conveyor being further provided with triggering means for tipping each individual cup or tray about its pivot over one of said collecting stations upon signals issued by said computer means in accordance with the predetermined features and properties of the object to be released from the cup or tray holding it.

22. Apparatus of claim 2, wherein said cups or trays, have a frusto-conical inner surface, for holding substantially spheroidal objects such as fruits and vegetables, or amorphous objects such as dates, soil clods, ore pieces and objects of similar shape.

23. Apparatus of claim 2, wherein said cups or trays, have a circular recess inner surface, for holding circular flat-bottomed or disc-shaped objects, such as containers, plates, wheels, tablets, cakes and objects of similar shape.

24. Apparatus of claim 2, further wherein revolving computer means, positioned on said inverter chainwheels, are interfaced to said actuators, sensor means, conditioning, amplification and signal processing electronics and stationary computer means.

25. Apparatus of claim 2, comprising slip rings positioned on the shaft of each of said inverter chainwheel sets, constituting means for power supply to said stepper motors, vibration actuators, revolving computer means and sensor conditioning and amplification electronics, as well as communication means between said revolving and stationary computer means.

* * * * *